United States Patent [19]
Moberg

[11] Patent Number: 5,425,750
[45] Date of Patent: Jun. 20, 1995

[54] ACCELEROMETER-BASED MULTI-AXIS PHYSICAL ACTIVITY SENSOR FOR A RATE-RESPONSIVE PACEMAKER AND METHOD OF FABRICATION

[75] Inventor: Sheldon B. Moberg, Granada Hills, Calif.

[73] Assignee: Pacesetter, Inc., Sylmar, Calif.

[21] Appl. No.: 91,850

[22] Filed: Jul. 14, 1993

[51] Int. Cl.⁶ .............................. A61N 1/365
[52] U.S. Cl. ........................... 607/19; 607/2; 607/17; 128/782; 73/517 R; 73/517 AV
[58] Field of Search ............ 607/2, 9, 19, 36, 17; 128/774, 782, 739, 740, 670; 310/348, 338, 339; 73/517 R, 517 AV

[56] References Cited
U.S. PATENT DOCUMENTS

| | | | |
|---|---|---|---|
| 4,140,132 | 2/1979 | Dahl | 128/419 PG |
| 4,305,396 | 12/1981 | Wittkampf et al. | 128/419 PG |
| 4,428,378 | 1/1984 | Anderson et al. | 128/419 PG |
| 4,686,988 | 8/1987 | Sholder | 128/419 PT |
| 4,712,555 | 12/1987 | Thornander et al. | 128/419 PG |
| 4,771,780 | 9/1988 | Sholder | 607/19 |
| 4,791,931 | 12/1988 | Slate | 128/419 PG |
| 4,860,751 | 8/1989 | Callaghan | 607/20 |
| 4,868,447 | 9/1989 | Lee et al. | 310/330 |
| 4,896,068 | 1/1990 | Nilsson | 310/330 |
| 4,920,801 | 5/1990 | Church | 73/517 R |
| 4,922,930 | 5/1990 | Adkins et al. | 607/19 |
| 4,969,359 | 11/1990 | Mikkor | 73/517 R |
| 5,014,700 | 5/1991 | Alt | 128/419 PG |
| 5,023,503 | 6/1991 | Legge et al. | 310/348 |
| 5,031,615 | 7/1991 | Alt | 128/419 PG |
| 5,040,534 | 8/1991 | Mann et al. | 128/419 PG |
| 5,040,535 | 8/1991 | Mann et al. | 128/419 PG |
| 5,044,366 | 9/1991 | Alt | 128/419 PG |
| 5,233,984 | 8/1993 | Thompson | 607/19 |
| 5,318,596 | 6/1994 | Barreras et al. | 607/19 |
| 5,330,510 | 7/1994 | Legay et al. | 607/19 |

OTHER PUBLICATIONS

Atochem Sensors, Inc. Product Brochure, *Standard and Custom Piezo Film Components*, pp. 1–10 (1991).
Bacharach, David W. et al., "Activity-Base Pacing: Comparison of a Device Using an Accelerometer Versus a Piezoelectric Crystal," *PACE*, vol. 15, pp. 188–196 (Feb. 1992).
Piezo Electric Products, Inc., "Piezoceramic Design Notes," *SENSORS* (Mar. 1984).
Salerno, David M. et al., "Seismocardiography: A New Technique for Recording Cardiac Vibrations. Concept, Method, and Initial Observations," *Journal of Cardiovascular Technology*, vol. 9, No. 2, 1990, pp. 111–118.
Salerno, David M. et al., "Seismocardiography for Monitoring Changes in Left Ventricular Function During Ischemia," *Chest*, vol. 100, pp. 991–993 (Oct. 1991).
Salerno, David M. et al., "Seismocardiographic Changes Associated With Obstruction of Coronary Blood Flow During Balloon Angioplasty," *The American Journal of Cardiology*, vol. 68, pp. 201–207 (Jul. 15, 1991).
Sandler, H. et al., "Miniature Implantable Accelerometers," pp. 165–174.

*Primary Examiner*—Kyle L. Howell
*Assistant Examiner*—Kennedy J. Schaetzle
*Attorney, Agent, or Firm*—Lisa P. Weinberg; Malcolm J. Romano

[57] ABSTRACT

An accelerometer-based, multi-axis physical activity sensor for use with a rate-responsive pacemaker, and a method for fabricating the sensor, are provided. The multi-axis physical activity sensor includes a cantilever beam having a film of a piezoelectric polymer adhered to each surface of an electrically conductive substrate. The piezoelectric films are highly resistant to fracturing during manufacture and in use, and they provide a strong output signal when stressed in response to bodily accelerations. A mass is mounted to a free end of the cantilever beam, and is substantially offset with respect to a planar surface of the beam so as to impart multi-axis sensitivity to the physical activity sensor. The accelerometer-based, multi-axis physical activity sensor provides an output signal that is communicated to pacemaker circuitry using a pair of electrical conductors.

40 Claims, 5 Drawing Sheets

ACCELEROMETER-BASED MULTI-AXIS PHYSICAL ACTIVITY SENSOR FOR A RATE-RESPONSIVE PACEMAKER AND METHOD OF FABRICATION

BACKGROUND OF THE INVENTION

This invention relates to cardiac stimulating devices and particularly to implantable cardiac stimulating devices capable of providing rate-responsive pacing therapy. More particularly, this invention is directed toward an accelerometer-based, multi-axis physical activity sensor for measuring levels to which a patient is engaged in physical activity, so that rate-responsive pacing therapy can be administered accordingly.

A pacemaker is an implantable medical device which delivers electrical stimulation pulses to cardiac tissue to relieve symptoms associated with bradycardia—a condition in which a patient cannot maintain a physiologically acceptable heart rate. Early pacemakers delivered stimulation pulses at regular intervals in order to maintain a predetermined heart rate, which was typically set at a rate deemed to be appropriate for the patient at rest. The predetermined rate was usually set at the time the pacemaker was implanted, and in more advanced devices, could be set remotely after implantation.

Early advances in pacemaker technology included the ability to sense a patient's intrinsic cardiac activity (i.e., the intercardiac electrogram, or "IEGM"). This led to the development of "demand pacemakers," so named because these devices deliver stimulation pulses only as needed by the heart. Demand pacemakers are capable of detecting a spontaneous, hemodynamically effective, cardiac contraction which occurs within a predetermined time period (commonly referred to as the "escape interval") following a preceding contraction. When a naturally occurring contraction is detected within the escape interval, a demand pacemaker does not deliver a pacing pulse. The ability of demand pacemakers to avoid delivery of unnecessary stimulation pulses is desirable, because it extends battery life.

Pacemakers such as those described above proved to be extremely beneficial in that they successfully reduced or eliminated seriously debilitating and potentially lethal effects of bradycardia in many patients. However, the early devices were not adjustable "in the field"—that is, the heart rates maintained by these devices were not adjustable in accordance with changing levels of physical exertion. Thus, during periods of elevated physical activity, some patients were subject to adverse physiological consequences, including lightheadedness and episodes of fainting, because their heart rates were forced by the pacemaker to remain constant at an inappropriately low rate. Also, some patients were subject to discomfort resulting from heart rates that were maintained higher than would normally be appropriate during periods of rest.

A major advance in pacemaker technology was the development of "rate-responsive pacemakers." These devices are capable of adjusting the patient's heart rate in accordance with metabolic demands, even as those demands vary as a result of changing levels of physical exertion. Rate-responsive pacemakers typically maintain a predetermined minimum heart rate when the patient is engaged in physical activity at or below a threshold level, and gradually increase the maintained heart rate in accordance with increased levels of physical activity until a maximum rate is reached. In many rate-responsive pacemakers, the minimum heart rate, maximum heart rate, and the slope or curve between the minimum heart rate and the maximum heart rate are programmable, so that they may be configured to meet the needs of a particular patient.

In order to provide rate-responsive pacing therapy, a pacemaker must be capable of correlating an indicator of physical activity to an appropriate heart rate. Past efforts to identify a reliable indicator of physical activity have led to the investigation of several physiological parameters—many of which have proven to be unsatisfactory in the context of rate-responsive pacing. Some of the physiological parameters that have been studied include central venous blood temperature, blood pH level, QT time interval, respiration rate, thoracic impedance, central venous oxygen saturation, stroke volume, and nerve activity. However, these indicators exhibit certain drawbacks with respect to their use in connection with rate-responsive pacing, including slow response time, excessive emotionally induced variations, and wide variability across individuals. Accordingly, these physiological indicators have not been widely applied in practice.

More generally accepted have been rate-responsive pacemakers which employ sensors that transduce mechanical forces associated with physical activity. A widely used sensor of this type incorporates a piezoelectric crystal which generates a measurable electrical potential when a mechanical stress resulting from physical activity is applied to the sensor. Dahl U.S. Pat. No. 4,140,132 and Anderson et al. U.S. Pat. No. 4,428,378 describe examples of rate-responsive pacemakers that maintain a patient's heart rate in accordance with physical activity as measured by a piezoelectric sensor.

Despite the widespread use of piezoelectric sensors in rate-responsive pacemakers, certain difficulties associated with their use have become apparent. For example, sensors that employ piezoelectric crystals typically provide extremely small output signals which are difficult to process. Also, assembly of a sensor incorporating a piezoelectric crystal is difficult because handling can cause stresses which exceed the tolerance limits of the crystal. The process of securing the sensor to a suitable supporting structure in the pacemaker can cause unacceptably high stresses, which can lead to fracturing of the crystal.

These and other difficulties related to the use of a piezoelectric sensor in a rate-responsive pacemaker were addressed in commonly assigned, copending U.S. patent application Ser. No. 08/059,698, filed May 10, 1993, entitled "A RATE-RESPONSIVE IMPLANTABLE STIMULATION DEVICE HAVING A MINIATURE HYBRID-MOUNTABLE ACCELEROMETER-BASED PHYSICAL ACTIVITY SENSOR FOR A RATE-RESPONSIVE PACEMAKER AND METHOD OF FABRICATION." That application describes a novel physical activity sensor that employs a resilient piezoelectric polymer in the transducing element. A cantilever beam of the sensor, which incorporates the piezoelectric polymer, is able to deflect to a greater extent than would be the case if a piezoelectric crystal was used and accordingly, the sensor provides a stronger output signal. Also, the resiliency of the piezoelectric polymer reduces the likelihood of fracturing during the fabrication process.

Despite the advances made as described in the commonly assigned, copending U.S. patent application mentioned above, certain additional difficulties have remained unaddressed. One of the most pressing of these difficulties is related to directional sensitivity—that is, physical activity sensors which have been widely used in the rate-responsive pacing context have been designed so as to be responsive to physical activity in directions along a single axis. U.S. Pat. No. 4,140,132 (Dahl), mentioned above, illustrates a sensor having such limited directional sensitivity—the axis of sensitivity being the one that projects from the patient's chest.

One of the main difficulties associated with the use of single-axis sensors is that they impose limitations on a physician's ability to choose the most appropriate axis of sensitivity for a particular patient. The common design choice has been the axis that projects from the patient's chest (as described above with respect to U.S. Pat. No. 4,140,132 (Dahl)). However, a physician may decide that another axis of sensitivity is more appropriate for a particular patient, for instance, in a case where a patient is frequently subjected, perhaps for occupational reasons, to externally induced forces in directions along the more commonly selected axis of sensitivity.

One might think that a typical prior art single-axis physical activity sensor could provide the desired flexibility if it were simply oriented in different directions as prescribed by a physician. Unfortunately, the solution is not so simple, mainly because of the frequently encountered problem of "twirler's syndrome"—a condition where the patient absent-mindedly manipulates the pacemaker implanted beneath the skin, thereby changing its orientation from time to time. If, for example, a single-axis sensor is initially positioned so as to be sensitive to physical activity in directions along the vertical axis (i.e., the axis extending along the length of the patient's body when the patient is standing), any twirling of the pacemaker will lead to a corresponding change to the axis of sensitivity, such that the new axis of sensitivity is likely to be one other than the vertical axis. Changes to the axis of sensitivity may lead to unexpectedly high or low measurements of physical activity which can cause the pacemaker to make inappropriate heart rate adjustments.

One concern that must always be kept in mind when designing pacemaker components is the need to conserve limited space available within the pacemaker. There is tremendous demand for implantable cardiac stimulating devices, including pacemakers, of reduced size but increased functionality. Thus, both the size and the number of components required to construct a physical activity sensor should be kept to minimum, and accordingly, any attempt to improve directional sensitivity should avoid the use of additional hardware components, including additional transducers or wires, to the greatest extent possible.

What is needed therefore is a physical activity sensor that is suitable for use with a rate-responsive pacemaker and which provides improved directional sensitivity. The improved sensor should overcome deficiencies associated with single-axis physical activity sensors, while minimizing the number of additional components required. In addition, the improved sensor should provide a relatively strong output signal and should be manufacturable in an efficient and cost-effective manner. Further, the sensor should be easy to secure to a suitable substrate—in particular, the pacemaker hybrid, so that the assembly and installation of the sensor can be conveniently integrated to the hybrid manufacturing process. The sensor should also be resistant to breakage, both during fabrication and in use.

SUMMARY OF THE INVENTION

The disadvantages and limitations of the prior art single-axis physical activity sensors described above are overcome by the present invention. With this invention, an accelerometer-based, multi-axis physical activity sensor for use with a rate-responsive pacemaker is provided, which is sensitive to bodily accelerations in directions along a plurality of axes, and more particularly, along two perpendicular axes. The physical activity sensor of the present invention thus advantageously provides improved directional sensitivity as compared to single-axis activity sensors known in the art. In addition, the physical activity sensor is resistant to fracturing during fabrication and in use, capable of providing a strong output signal, and manufacturable in an efficient, cost-effective manner.

In the preferred embodiment, the sensor is constructed as a cantilever beam having a film of a piezoelectric polymer adhered to each surface of an electrically conductive substrate. On a free end of the cantilever beam is a mass which is mounted so as to be substantially offset with respect to the planar surface of the beam. This arrangement permits the sensor to be responsive to bodily accelerations associated with physical activity in directions along two perpendicular axes. More particularly, the multi-axis physical activity sensor of the present invention provides an output signal when subjected to accelerations along the axis that is perpendicular to the planar surface of the cantilever beam, as well as to accelerations along the axis that is parallel to the longer length of the cantilever beam.

The improved directional sensitivity provided by the multi-axis physical activity sensor is particularly advantageous when it is desirable to avoid measuring physical activity based on bodily accelerations along the axis that projects from the patient's chest. When such a configuration is desirable for a particular patient, multi-axis sensitivity permits the physical activity sensor to provide a significant output signal despite manipulation of the pacemaker by the patient.

Although the physical activity sensor of the present invention provides multi-axis sensitivity to bodily accelerations, it generates a signal which is communicated to processing circuitry within the pacemaker through only one pair of electrical conductors. By minimizing the number of electrical conductors required for the sensor, the overall number of components which need to be included within the pacemaker housing is advantageously reduced. Also, there is no need to include any circuitry or programming to combine separately conducted output signals.

In a preferred embodiment, the multi-axis physical activity sensor is suitably mounted within the pacemaker so as to be responsive to bodily accelerations associated with physical activity. The sensor can also be mounted externally, or even remotely—for example, on or within a pacing lead. Bodily accelerations experienced by the sensor (i.e., those having components along the axes of sensitivity) cause the free end of the cantilever beam to deflect, which results in measurable electrical potentials appearing across the surfaces of the beam. The induced electrical potentials are indicative of the levels to which the patient is engaged physical activity.

The use of a piezoelectric polymer in the accelerometer-based, multi-axis physical activity sensor of the present invention offers several advantages over other known transducing materials, such as piezoelectric crystals. The piezoelectric polymer is extremely resilient, which facilitates the fabrication process and improves performance in the field. During fabrication of the multi-axis physical activity sensor of the present invention, and during installation of the sensor within a pacemaker, the resiliency of the piezoelectric polymer reduces the likelihood of fracturing during handling. Thus, manufacturing procedures may be performed in a more efficient, cost-effective manner.

In the field, the multi-axis physical activity sensor of the present invention provides a comparatively strong output signal because the sensor is designed to experience stresses of greater magnitude than other known sensors, owing to the resiliency of the piezoelectric polymer. As is known in the art, the magnitude of the output signal from a sensor that uses a piezoelectric material varies in accordance with the magnitude of the stresses experienced by the material. Since the piezoelectric polymer is more resilient than, for example, a piezoelectric crystal, the sensor may be designed so that the polymer is stressed to a greater extent, and accordingly, the output signal is much stronger. To illustrate, the sensor of the present invention provides output of about 1 volt/G, whereas some known single-axis physical activity sensors that use piezoelectric crystals provide output on the order of about 10 millivolts/G.

In another aspect of the present invention, a method of fabricating the accelerometer-based, multi-axis physical activity sensor as described above is provided.

The output signal provided by the accelerometer-based, multi-axis physical activity sensor of the present invention is communicated to circuitry within a rate-responsive pacemaker, which may be otherwise conventional. The output signal is used by processing circuitry to determine the level to which the patient is engaged in physical activity, and to correlate the determined level of physical activity to a desired heart rate. The processing circuitry causes pulse generating circuitry to maintain the patient's heart rate at the desired rate, preferably by adjusting the escape interval. Pacing pulses are provided by pacing leads, which also may be conventional.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE PREFERRED EMBODIMENTS

Figure 1:
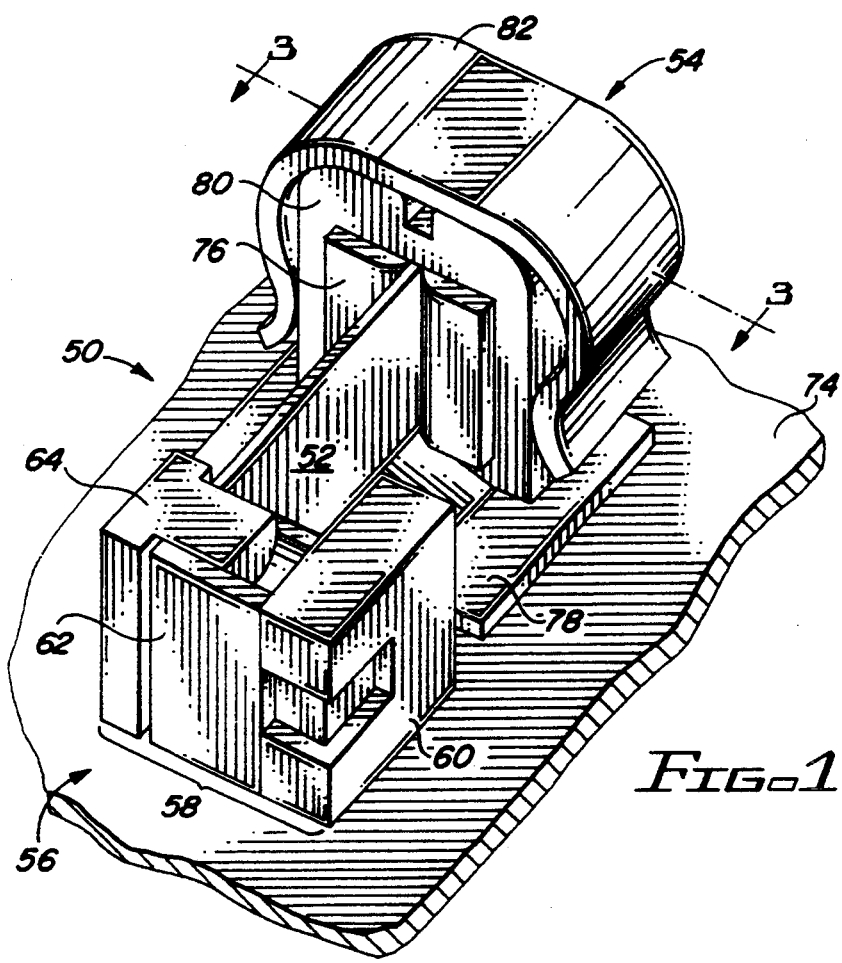
FIG. 1 is a perspective view of a preferred embodiment of an accelerometer-based, multi-axis physical activity sensor in accordance with the principles of the present invention.

Referring to FIG. 1, a preferred embodiment of an accelerometer-based, multi-axis physical activity sensor 50 for use with a rate-responsive pacemaker (not shown in FIG. 1) in accordance with the principles of the present invention is described. In the preferred embodiment of the invention, a weighted cantilever beam 52 serves as the transducing element for the sensor 50, and is capable of transducing bodily accelerations associated with physical activity occurring in directions along a plurality of axes (in a manner described in greater detail below).

The cantilever beam 52, which in the preferred embodiment has a length of about 0.150 inches, a width of about 0.050 inches, and a thickness of about 0.0025 inches, has a fixed end 54 and a free end 56. The free end 56 deflects in response to bodily accelerations, while the fixed end 54 remains secured in place. The magnitude of the deflections experienced by the free end 56 of the cantilever beam 52 varies in accordance with the magnitude of the bodily accelerations experienced by the sensor 50. However, in the preferred embodiment, an offset mass assembly 58 is affixed to the free end 56 of the cantilever beam 52 in order to enhance the magnitude of the deflections, thereby causing the sensor 50 to provide a stronger output signal. In addition, the offset mass assembly 58 imparts multi-axis sensitivity to the sensor 50 (as described in greater detail below).

The offset mass assembly 58 may be constructed in a variety of ways. In the preferred embodiment, the offset mass assembly 58 includes a mass 60 which is supported on the cantilever beam 52 by a mass mount 62 and a mass backing 64. The mass 60 preferably has a length of about 0.050 inches, a width of about 0.080 inches, and a thickness of about 0.020 inches (as measured along the dimensions corresponding to the cantilever beam 52). The mass preferably weighs about 13 milligrams, and is made from a dense, non-ferrous, and relatively inexpensive material, such as tungsten. The mass mount 62 and the mass backing 64 are made from a light plastic material, such as polycarbonate, so that most of the weight of the offset mass assembly 58 is attributable the mass 60.

Figure 2:
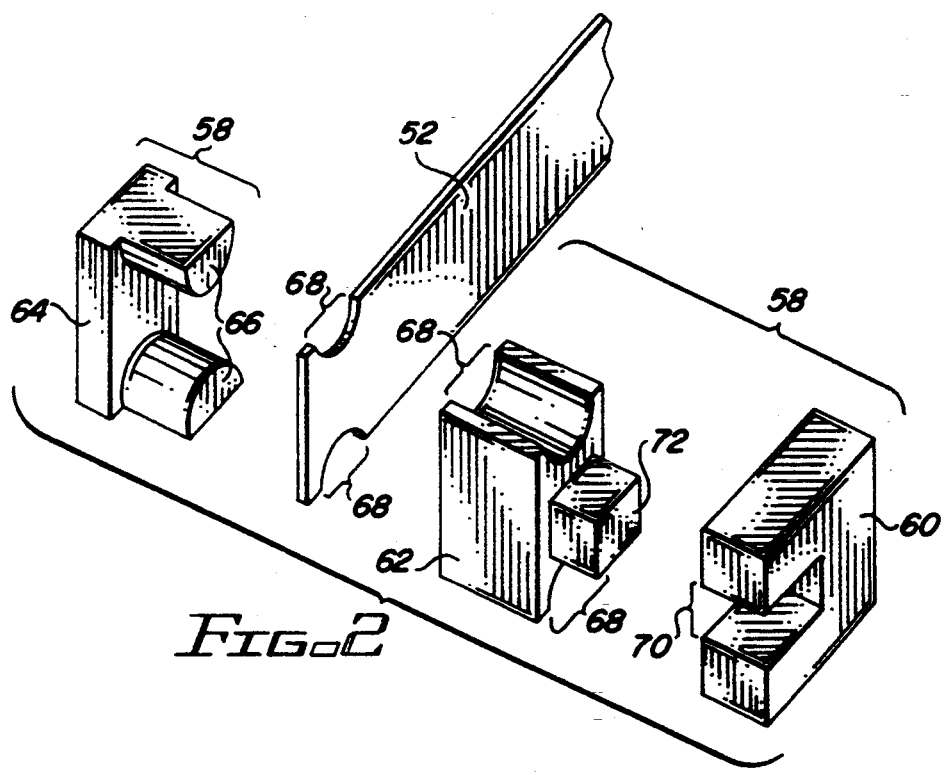
FIG. 2 is an exploded, perspective view of a cantilever beam and an offset mass assembly of the accelerometer-based, multi-axis physical activity sensor shown in FIG. 1.

The manner by which the mass assembly 58 is secured to the free end 56 of the cantilever beam 52 may be understood by reference to FIG. 2, in which the free end 56 of the cantilever beam 52, the mass 60, the mass mount 62, and the mass backing 64 are shown as they may appear prior to sub-assembly of the mass assembly 58. The mass backing 64 is shaped so as to have a pair of semicylindrical protrusions 66. The free end 56 of the cantilever beam 52 and the mass mount 62 each have a pair of indentations 68 which correspond to the shape of the semicylindrical protrusions 66 of the mass backing 64.

When the components of the mass assembly 58 are secured together with a suitable adhesive, the cantilever beam 52 is disposed between the mass mount 62 and the mass backing 64. The semicylindrical protrusions 66 register with the corresponding indentations 68 of the cantilever beam 52 and the mass mount 62. This arrangement causes the cantilever beam 52 to be effectively locked into the mass assembly 58. The interlocking construction as shown in FIG. 2 improves safety and reliability, because the possibility of an output signal interruption or reduction resulting from unexpected slippage of the cantilever beam 52 from the mass assembly 58 is substantially reduced.

The mass 60 has a notch 70 which corresponds in shape to a protrusion 72 that extends from the mass mount 62. To secure the mass 60 to the mass assembly 58, the protrusion 72 is inserted into the notch 70. A suitable adhesive is used to ensure that the mass 60 does not become dislodged from the mass mount 62. After the mass assembly 58 is secured to the cantilever beam 52, the distance between the cantilever beam 52 and the center of gravity of the mass 60 is preferably about 0.030 inches.

Figure 3:
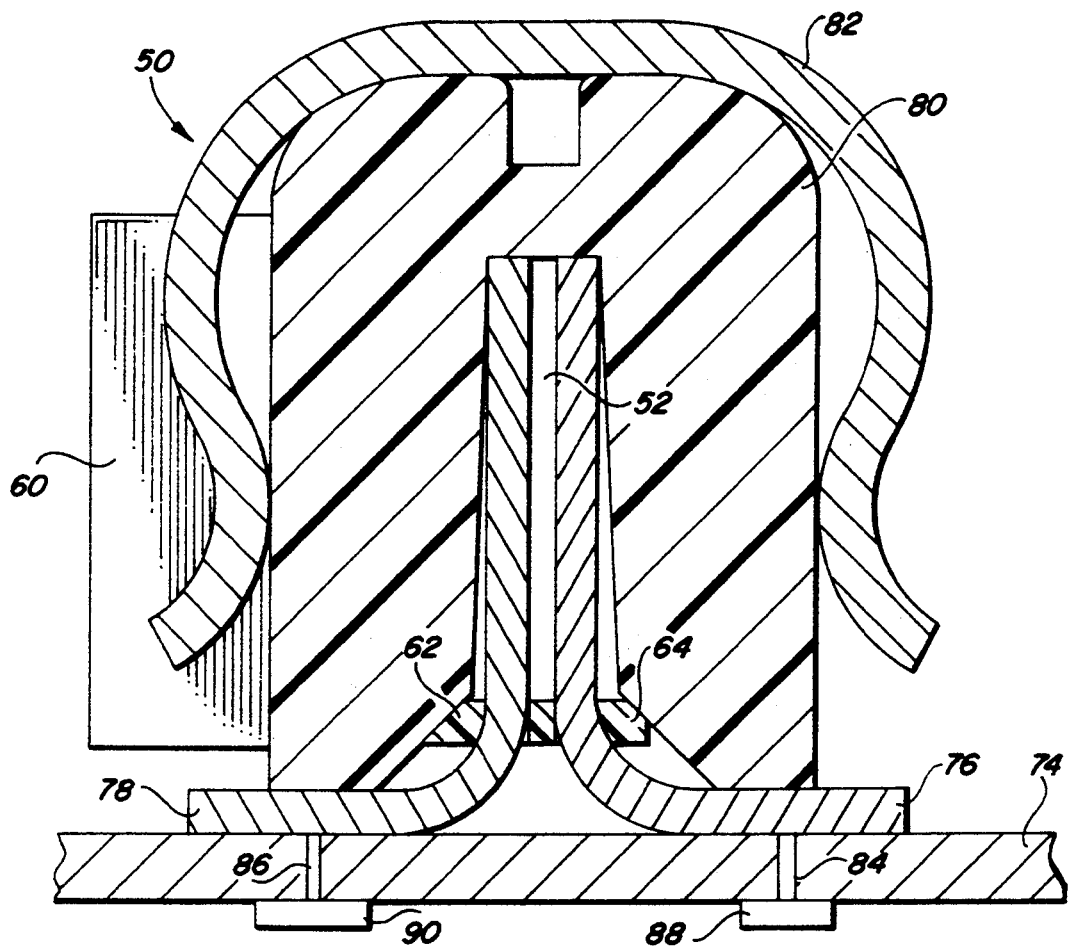
FIG. 3 is a cross-sectional view of the accelerometer-based, multi-axis physical, activity sensor, taken along line 3—3 of FIG. 1.

Referring again to FIG. 1, and by reference to the cross-section shown in FIG. 3, the manner by which the fixed end 54 of the cantilever beam 52 is secured to a suitable substrate 74 is described. In one preferred embodiment (described in greater detail below), the substrate 74 may be a pacemaker hybrid (not shown in FIGS. 1 and 3), and fabrication of the sensor 50 may thus be conveniently integrated into the hybrid manufacturing process. Alternatively, the substrate 74 may be separate from the pacemaker hybrid, to allow for mounting of the sensor 50 to another suitable location within or on the pacemaker, for example, to a battery support (also described in greater detail below). When the sensor 50 is not mounted directly on the pacemaker hybrid, a ceramic material such as alumina may be used to form the substrate 74.

As previously mentioned, the cantilever beam 52 is the transducing element of the sensor 50. The manner by which the cantilever beam 52 is secured at its fixed end 54, and by which electrical connections are made between the cantilever beam 52 and the pacemaker circuitry, allows the sensor 50 of the present invention to be efficiently constructed using a minimal number of components.

A pair of electrically conductive supports 76 and 78 are adhered to the substrate 74. Beryllium copper is a suitable material from which the supports 76 and 78 may be fabricated, because it is highly conductive and relatively strong. Each of the pair of supports 76 and 78 is shaped so as to include three regions which are orthogonally oriented with respect to one another. A first region of each of the pair of supports 76 and 78 is adhered to the substrate 74, while second and third regions of each of the pair of supports 76 and 78 project from the substrate 74.

A mount 80, made from a light plastic material such as polycarbonate, is placed over the pair of supports 76 and 78 such that one of the regions of each of the pair of supports 76 and 78 contact, respectively, one of the interior surfaces of the mount 80, while a second region of each of the pair of supports 76 and 78 contact the surface of the mount 80 that faces the offset mass assembly 58. In this configuration, the pair of supports 76 and 78 form a slot within which the fixed end 54 of the cantilever beam 52 is disposed.

A retaining clip 82 is placed over the mount 80 to urge the interior surfaces of the mount 80, and the regions of the pair of supports 76 and 78 adhered thereto, against the surfaces of the cantilever beam 52. Beryllium copper has a relatively high spring constant, and is thus a suitable material from which the retaining clip 82 may be fabricated. Through the arrangement shown in FIGS. 1 and 3, a stable electrical connection is established between each surface of the cantilever beam 52 and one of the pair of supports 76 and 78, while at the same time, the cantilever beam 52 is securely positioned in an orthogonal orientation with respect to the substrate 74. Thus, the pair of supports 76 and 78 advantageously minimize the number of required components by serving two purposes—they communicate an electrical signal generated by the cantilever beam (as described in greater detail below) to circuitry (not shown in FIGS. 1 and 3) within the pacemaker, and they also mechanically support the cantilever beam in its proper position.

The embodiment of the sensor 50 depicted in FIG. 3 includes certain components which are used when the substrate 74 is separate from the pacemaker hybrid (not shown in FIG. 3), so that the signal provided by the sensor 50 may be conducted to processing circuitry (not shown in FIG. 3) within the pacemaker. The substrate 74 includes a pair of conductor-filled conduits 84 and 86 which connect the pair of supports 76 and 78 to a pair of electrically conductive contact pads 88 and 90, respectively. A pair of wires (not shown in FIG. 3) for conducting the signal provided by the sensor 50 to the pacemaker processing circuitry may be wire-bonded (or otherwise suitably adhered) to the pair of contact pads 88 and 90. If the pacemaker hybrid serves as the substrate 74, the pair of supports 76 and 78 are adhered to a pair of electrically conductive traces (not shown) on the hybrid, and accordingly, the pair of conductor-filled conduits 84 and 86 and the pair of contact pads 88 and 90 are not necessary.

Figure 4:
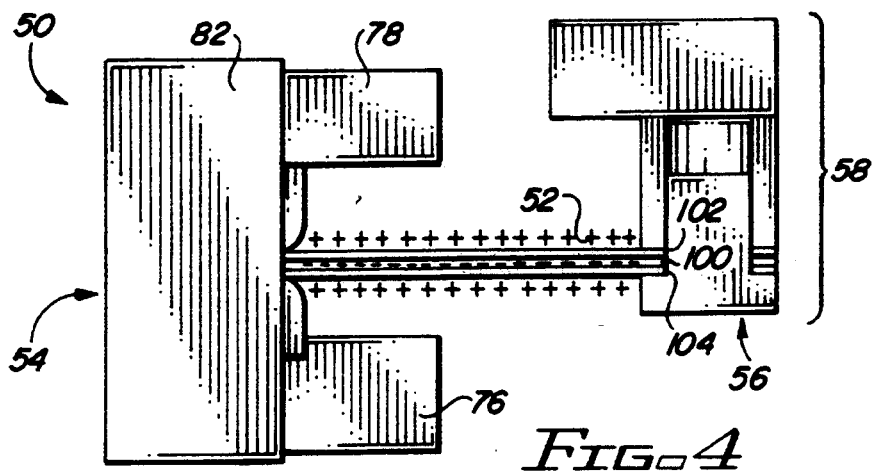
FIG. 4 is a top view of the accelerometer-based, multi-axis physical activity sensor shown in FIG. 1, depicting a cantilever beam of the physical activity sensor in a resting state.
Figure 5:
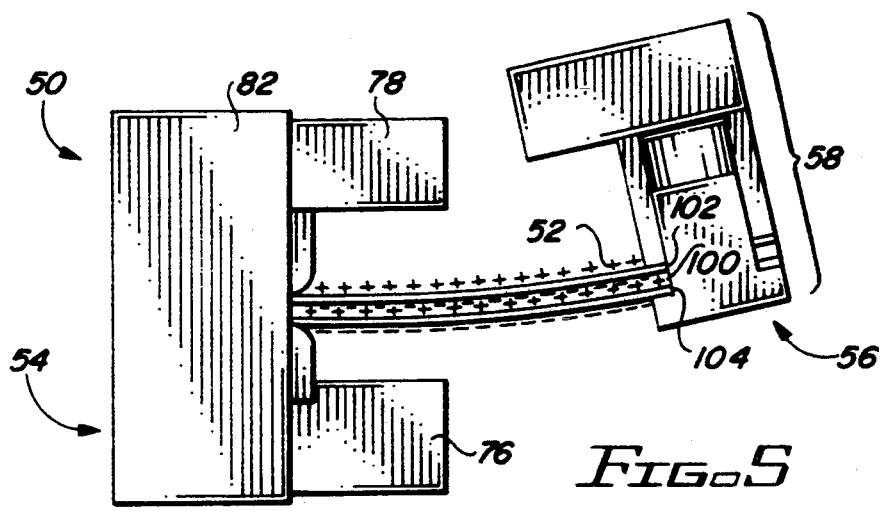
FIG. 5 is another top view of the accelerometer-based, multi-axis physical activity sensor shown in FIG. 1, depicting an induced potential across a cantilever beam of the physical activity sensor resulting from a deflection of the cantilever beam in a first direction.
Figure 6:
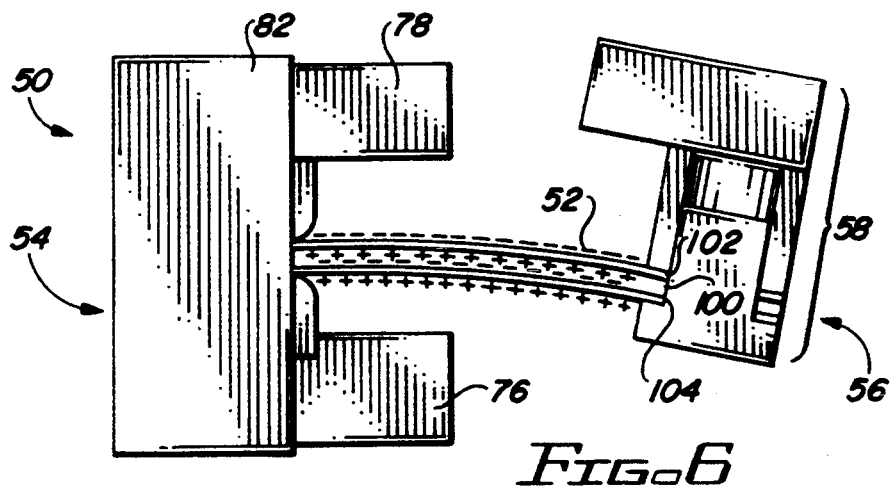
FIG. 6 is another top view of the accelerometer-based, multi-axis physical activity sensor shown in FIG. 1, depicting an induced potential across a cantilever beam of the physical activity sensor resulting from a deflection of the cantilever beam in a second direction.

The manner by which the sensor 50 responds to bodily accelerations associated with physical activity may be understood by reference to FIGS. 4–6 (for clarity, the substrate 74 has not been included in FIGS. 4–6). In order to provide an output signal representative of bodily accelerations, the cantilever beam 52 incorporates a material having an electrical characteristic that varies measurably in response to mechanical stresses experienced by the cantilever beam 52. The mechanical stresses are the result of conformational changes caused by bodily accelerations associated with physical activity.

In the preferred embodiment shown in FIGS. 4–6, the cantilever beam 52 is constructed from a beam substrate 100 having a first transducing layer 102 laminated to a first surface of the cantilever beam 52 and a second transducing layer 104 laminated to a second surface of the cantilever beam 52. The substrate 100 is formed from an electrically conductive metal, such as beryllium copper. The first and second transducing layers 102 and 104 are preferably films of a piezoelectric polymer, such as polyvinylidene fluoride (commonly known by the trademark KYNAR, owned by ATOCHEM North America). The first and second transducing layers 102 and 104 are in electrical contact with the supports 78 and 76, respectively. As previously described, the retaining clip 82 urges the pair of supports 76 and 78 against the surfaces of the cantilever beam 52, by applying a compressional force against the sides of the mount 80 (not visible in FIGS. 4–6, but shown in FIGS. 1 and 3).

The electrical configuration shown in FIGS. 4–6, in which the transducing layers 102 and 104 are connected in series, is preferred because it simplifies the fabrication process and allows the sensor 50 to provide a relatively strong output signal. The transducing layers 102 and 104 may instead be connected in a parallel configuration (not shown). This could be accomplished by commonly connecting the pair of supports 76 and 78, and measuring the potentials between the commonly connected pair of supports 76 and 78 and the beam substrate 100. However, the parallel configuration would require an additional electrical connection to the beam substrate 100, which may add complexity to the fabrication process.

Although in the preferred embodiment the cantilever beam 52 is constructed as a piezoelectric bimorph with a beam substrate 100, other configurations are possible. For example, the cantilever beam 52 may be constructed with a piezoelectric film on only one surface of the beam substrate 100, thereby forming a piezoelectric monomorph (not shown). Alternatively, the cantilever beam 52 may be constructed as another type of piezoelectric bimorph (not shown), in which two piezoelectric films are adhered to one another and are not separated by a beam substrate. However, it is preferable to include the beam substrate 100 when fabricating the cantilever beam 52, because it impedes deformation of the transducing layers 102 and 104 which may otherwise occur over time.

The use of a piezoelectric polymer offers several advantages as compared to materials used in other physical activity sensors known in the art. For example, the first and second transducing layers 102 and 104 made from a piezoelectric polymer are extremely resilient as compared to, for example, piezoelectric crystals, and are thus less likely to fracture during fabrication and in use. Also, the resiliency of the first and second transducing layers 102 and 104 advantageously enables the cantilever beam 52 to deflect to a much greater extent than would be the case if piezoelectric crystals were used. Thus, the sensor 50 of the present invention is capable of providing output of about 1 volt/G, while many prior art physical activity sensors are limited to providing output of up to about 10 millivolts/G. The strong output signal provided by the sensor 50 is thus more easily distinguishable over noise.

FIG. 4 depicts the cantilever beam 52 as it appears during a resting state of the sensor 50 (no motion). During construction of the cantilever beam 52, the first and second transducing layers 102 and 104 are polarized such that one surface of each layer has a positive charge and the other surface of each layer has a negative charge. As shown in FIG. 4, the first and second transducing layers 102 and 104 are adhered to the beam substrate 100 such that each negatively charged surface makes contact with the beam substrate 100. Thus, in the resting state of the sensor 50, there is no potential difference between the pair of supports 76 and 78.

FIG. 5 shows a change in polarization of the second transducing layer 104 during a deflection of the free end 56 of the cantilever beam 52 in a first direction, caused by an acceleration experienced by the sensor 50. As the second transducing layer 104 is bent in the first direction, its polarization inverts, causing a negative charge to appear on the surface of the cantilever beam 52 that contacts the support 76, while the first transducing layer 102 retains a positive charge on the surface that contacts the support 78. Thus, an overall positive potential is measurable between the pair of supports 76 and 78 (with the support 78 taken as the positive contact). The magnitude of the positive potential varies in accordance with the extent of the deflections in the first direction.

FIG. 6 shows a change in polarization of the first transducing layer 102 during a deflection of the free end 56 of the cantilever beam 52 in a second direction (opposite to that shown in FIG. 5). As the first transducing layer 102 is bent in the second direction, the polarization of the first transducing layer 102 inverts, causing a negative charge to appear on the surface of the cantilever beam 52 in contact with the support 78, while the second transducing layer 104 retains a positive charge on the surface in contact with the support 76. Thus, an overall negative potential is measurable between the pair of supports 76 and 78 (again, with the support 78 taken as the positive contact). The magnitude of the negative potential varies in accordance with the extent of the deflections in the second direction.

As previously mentioned, a particularly important feature of the sensor 50 of the present invention is that it provides multi-axis sensitivity—specifically, the sensor 50 is responsive to bodily accelerations associated with physical activity in directions along a plurality of axes. Thus, the deflections (and resulting potentials) described in connection with FIGS. 4–6 may be induced by bodily accelerations in a wider range of directions than would be the case for a single-axis physical activity sensor.

Improved directional sensitivity is provided by the arrangement of the mass assembly 58 with respect to the cantilever beam 52. In particular, the mass 60 is secured to the cantilever beam 52 (by the mass mount 62 and the mass backing 64) so as to be substantially offset with respect to the planar surface of the cantilever beam 52, as described with respect to FIGS. 1 and 2. This design allows the sensor 50 to respond to bodily accelerations along the axis that is parallel to the longer length of the cantilever beam 52, as well as the axis that is perpendicular to the planar surface of the cantilever beam 52.

In a preferred configuration, the sensor 50 is mounted to a pacemaker (not shown in FIGS. 4–6) so that the longer length of the cantilever beam 52 is parallel to the axis extending from left side to right side of the pacemaker, and that the planar surface of the cantilever beam 52 is perpendicular to the vertical axis of the pacemaker. If a single-axis sensor was mounted in this configuration, an occurrence of "twirler's syndrome" could cause a substantial variation in the output signal. In contrast, the sensor 50 of the present invention would provide significant output despite manipulation of the pacemaker, because it provides greater directional sensitivity.

Also of particular importance is that the sensor 50 provides multi-axis sensitivity while using only two electrical conductors (the supports 76 and 78) to conduct the signal to processing circuitry in the pacemaker (not shown in FIGS. 4–6). This feature advantageously reduces the number of components required to construct the sensor, and also simplifies the circuitry required to process the output signal.

Figure 7:
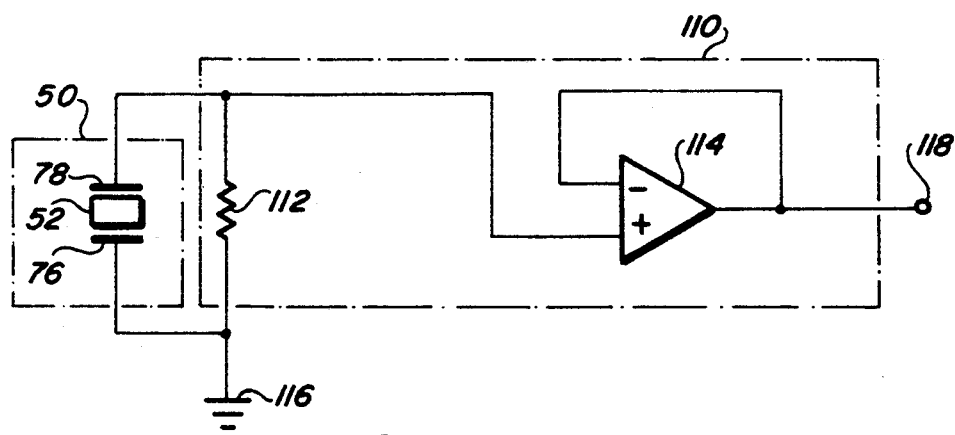
FIG. 7 is a schematic diagram of signal processing electronics used to initially process the raw signal provided by the accelerometer-based, multi-axis physical activity sensor shown in FIG. 1 in accordance with the principles of the present invention.

Referring now to FIG. 7, an electronic circuit 110 is shown for initially processing the output signal provided by the physical activity sensor 50 described with respect to FIGS. 1–6. A processing circuit 110 is preferably included on the hybrid of the pacemaker (not shown in FIG. 7). The sensor 50 is schematically illustrated as including only the cantilever beam 52 and the pair of supports 76 and 78. It should be understood that the raw output signal being initially processed by the circuit 110 is the varying potential that appears across the cantilever beam 52 in the manner described with respect to FIGS. 4–6. It should also be understood that other components (such as the pair of conductor-filled conduits 84 and 86 and the pair of contact pads 88 and 90 shown in FIG. 3) may intercede between the sensor 50 and the circuit 110, depending on how the sensor 50 is secured to the pacemaker.

In the preferred embodiment, the support 78 (which contacts the first transducing layer 102 as shown in FIGS. 4–6) is connected to one end of a resistor 112 and also to the noninverting input of an operational amplifier 114. The support 76 (which contacts the second transducing layer 104 as shown in FIGS. 4–6) and the other end of the resistor 112 are connected to a ground node 116. The output from the operational amplifier 114 is fed back to its inverting input. The operational amplifier 114 is, of course, an active element, and is supplied with power from a power supply (not shown) within the pacemaker. The resistor 112 has a high value of resistance, preferably about 22 gigohms, so that the processing circuit 110 serves as a filter, the output of which taken at an output terminal 118, is limited to frequency components associated with bodily accelerations. The signal at the output terminal 118 is provided to other circuitry (not shown in FIG. 7) in the pacemaker for correlating physical activity to heart rate.

Figure 8:
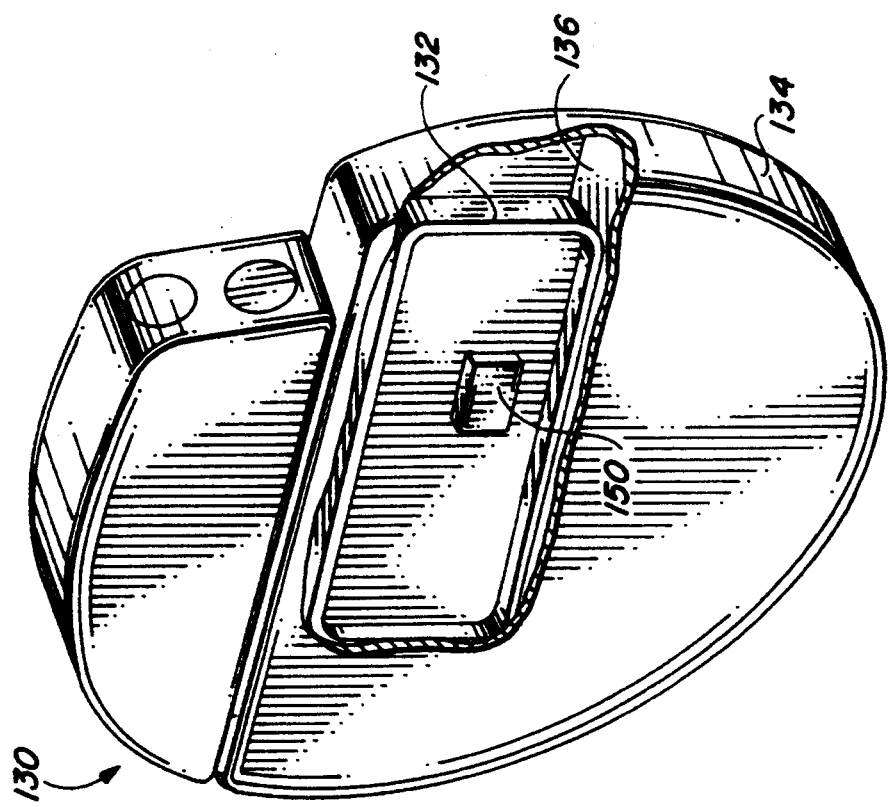
FIG. 8 is a partial cutaway view of a rate-responsive pacemaker having an accelerometer-based, multi-axis physical activity sensor mounted to a hybrid in accordance with the principles of the present invention.

Referring now to FIG. 8, a portion of the interior of a pacemaker is shown to illustrate a preferred mounting location for a physical activity sensor in accordance with the principles of the present invention. In FIG. 8, a pacemaker 130 is shown having a hybrid 132 disposed within an implantable housing 134. A battery 136 is disposed within the lower portion of the implantable housing 134. The pacemaker 130 may include other components, but they are not pertinent in the present context.

The hybrid 132 supports circuitry (not shown in FIG. 8) which allows the pacemaker to provide rate-responsive pacing therapy to a patient (not shown). In this preferred embodiment, a sensor 150 (schematically depicted as a block in FIG. 7 and not drawn to scale) is bonded to a surface of the hybrid 132. The sensor 150 is constructed in a manner substantially as described for the sensor 50 of FIGS. 1–6. In this configuration, the hybrid 132 serves the purpose described for the substrate 74 of FIG. 1. The hybrid 132 has conductive traces (not shown) deposited thereon, and the sensor 150 has a pair of electrically conductive supports (not shown, but similar to the pair of supports 76 and 78 of FIGS. 1 and 3–6) which contact the conductive traces. The sensor 150 may optionally be enclosed within a suitable housing (not shown). Mounting the sensor 150 to the hybrid 132 is advantageous, because assembly and installation of the sensor 150 may be incorporated into the fabrication process of the hybrid 132.

Figure 9:
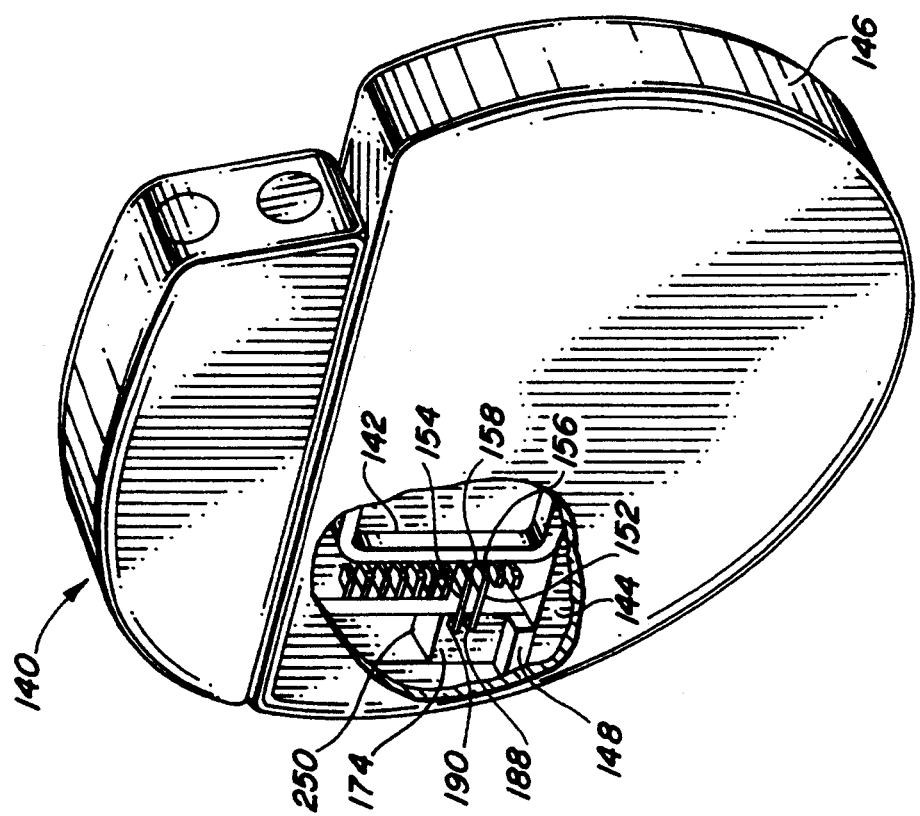
FIG. 9 is a partial cutaway view of a rate-responsive pacemaker having an accelerometer-based, multi-axis physical activity sensor disposed within a battery support in accordance with the principles of the present invention.

An alternative mounting location for the physical activity sensor of the present invention is shown in FIG. 9. To illustrate this embodiment, a pacemaker 140 is shown having a hybrid 142 and a battery 144 disposed within an implantable housing 146. The pacemaker 140 also includes a battery support 148 which is adhered to the interior of the pacemaker 140 and serves to secure the battery 144 within the implantable housing 146.

The battery support 148 includes a cavity which contains a sensor 250 constructed in a manner substantially as described for the sensor 50 of FIGS. 1–6. A substrate 174 (similar to the substrate 74 of FIG. 1), upon which the sensor 250 is mounted, has two conductor-filled conduits (not shown, but similar to the pair of conductor-filled conduits 84 and 86 of FIG. 3) for electrically connecting first and second supports (not shown, but similar to the pair of supports 76 and 78 of FIGS. 1 and 3–6) to a pair of contact pads 188 and 190 (similar to the pair of contact pads 88 and 90 of FIG. 3) adhered to the exterior surface of the substrate 174. A pair of wires 152 and 154 are used to connect the contact pads 188 and 190 to a pair of terminals 156 and 158 on the hybrid 142. Circuitry (not shown in FIG. 9) on the hybrid 142 is thereby provided with an output signal from the sensor 250, which may be subsequently processed and used by the pacemaker 140 to provide rate-responsive pacing therapy.

Figure 10:
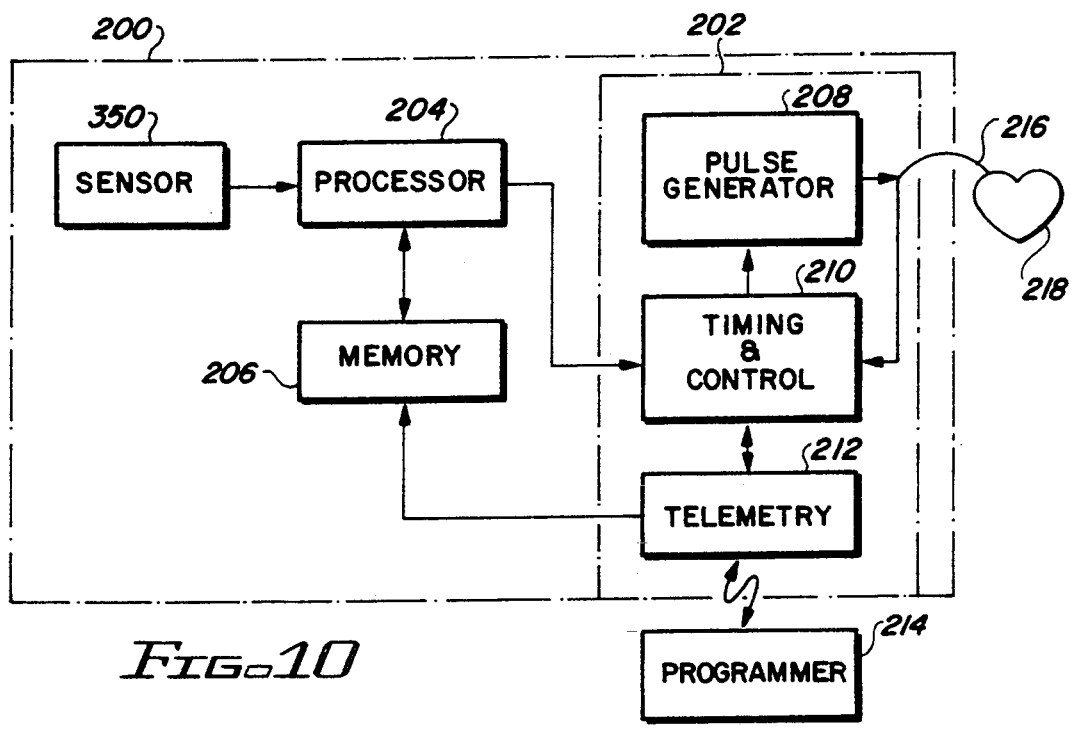
FIG. 10 is a schematic block diagram of a rate-responsive pacemaker including an accelerometer-based, multi-axis physical activity sensor in accordance with the principles of the present invention.

Referring now to FIG. 10, a block diagram illustrating the operation of a pacemaker 200 that uses a signal representative of physical activity provided by a multi-axis physical activity sensor 350 is described. The sensor 350 is constructed in a manner substantially as described for the sensor 50 of FIGS. 1–6. The pacemaker 200 includes a pacemaker circuit 202 (which may be conventional), the multi-axis physical activity sensor 350, a processor 204 coupled to the sensor 350, and a memory circuit 206 coupled to processor 204. Although the sensor 350 is depicted to be within the pacemaker 200 (for example, positioned at one of the preferred locations shown in FIGS. 8 and 9), the sensor 350 may alternatively be externally located, and indeed, may even be remotely located, such as at a suitable location on or within a pacing lead.

The pacemaker circuit 202 includes a pulse generator circuit 208, a timing and control circuit 210 coupled to the pulse generator circuit 208 and to the processor 204, and a telemetry circuit 212. The telemetry circuit 212 telemetrically communicates with an external programmer 214, and is coupled within the pacemaker 200 to the memory circuit 206 and the timing and control circuit 210.

Coupled to the pulse generator circuit 208 is at least one pacing lead 216, which may be conventional. The pacing lead 216 is used to deliver pacing pulses provided by the pulse generator circuit 208 to a patient's heart 218. In addition, the pacing lead 216 senses intrinsic activity of the heart 218, and presents a signal indicative thereof to the timing and control circuit 210. Thus, the pacemaker 200 is capable of operating in a "demand mode," in which delivery of a pacing pulse is inhibited by the timing and control circuit 210 when an intrinsic cardiac contraction is sensed during the escape interval following a preceding contraction.

Although the following description assumes that the pacemaker 200 is operating in a demand mode, it should be understood that a simpler implementation is possible, in which the pacemaker 200 does not inhibit delivery of pacing pulses when intrinsic contractions are sensed, but still changes the patient's heart rate in response to the output of the sensor 350. Also, a demand mode may be a telemetrically programmable feature, allowing the pacemaker 200 to be switched into and out of demand mode when desired by a physician.

In operation, the sensor 350 responds to bodily accelerations associated with physical activity in directions along a plurality of axes. A sensor signal is generated by the sensor 350, which is indicative of the level to which the patient is engaged in physical activity. For the purposes of this discussion, the processing circuit 110 described with respect to FIG. 7 is assumed to be incorporated within the sensor 350, although other arrangements are possible. The sensor signal is provided to the processor 204, which further processes the sensor signal using techniques which may be conventional (e.g., averaging, half-wave rectification, full-wave rectification) to determine a current level of physical activity. The processor 204 in turn provides a rate control signal to the timing and control circuit 210, which determines the heart rate to be maintained by the pacemaker 200. In a preferred embodiment, the rate control signal provided by the processor 204 adjusts the escape interval used by the timing and control circuit 210, which has the effect of increasing or decreasing the maintained heart rate. It should be noted that the pacemaker 200 can also be telemetrically programmed by the programmer 214 to operate in a constant rate mode if desired by the physician.

Figure 11:
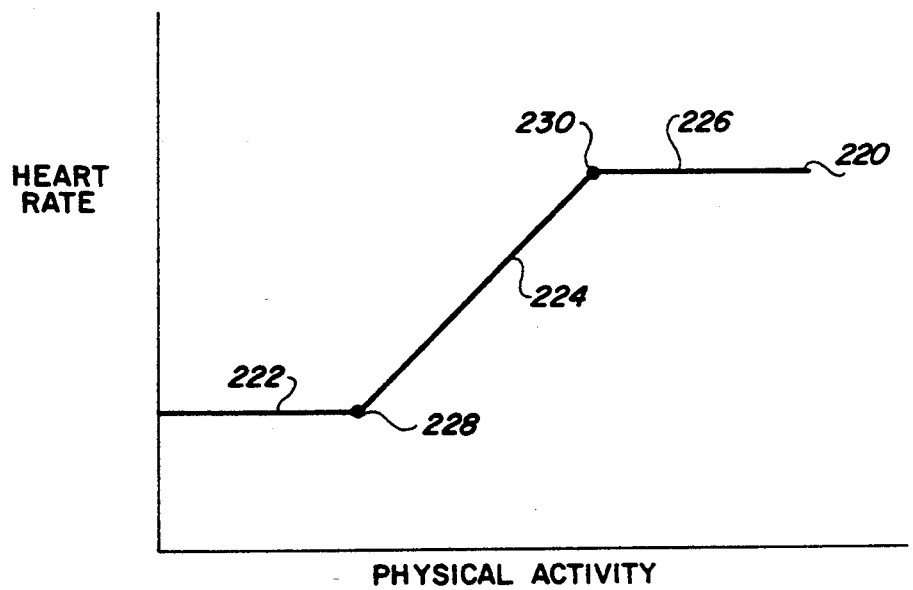
FIG. 11 depicts a representative transfer curve used by a rate-responsive pacemaker in accordance with the principles of the present invention.

The manner by which the pacemaker 200 adjusts the maintained heart rate in accordance with a signal provided by the multi-axis physical activity sensor 350 of the present invention may be understood by reference to a transfer curve 220 shown in FIG. 11. The transfer curve 220 correlates physical activity (as measured by the sensor 350 of FIG. 10) along the horizontal axis with a desired heart rate along the vertical axis. The transfer curve 220 has three segments—a minimum rate segment 222, a slope segment 224, and a maximum rate segment 226, each of which may be telemetrically varied to meet the needs of a particular patient. For example, a physician (not shown) may set the minimum rate segment 222 at 60 beats per minute, and may set a first activity threshold 228 at a relatively low level of physical activity that is required before the pacemaker 200 (FIG. 10) abandons the heart rate defined by the minimum rate segment 222 in favor of a heart rate determined by the slope segment 224. The physician may set the maximum rate segment 226 at, for example, 120 beats per minute, and may set a second activity threshold 230 at a relatively high level of physical activity that is required before the pacemaker 200 (FIG. 10) discontinues using the slope segment 224 in favor of the heart rate corresponding to the maximum rate segment 226. In addition, the slope segment 224 may be telemetrically adjustable, so that changes to the maintained heart rate may be more gradual or more aggressive, depending upon the needs of a particular patient.

Information defining the transfer curve 220 is stored in the memory 206 (FIG. 10) of the pacemaker 200 (FIG. 10) in a conventional manner. For example, the transfer curve 220 may be stored as a collection of discrete data points in a look-up table (not shown). Alternatively, the minimum rate segment 222 and the maximum rate segment 226 may be stored discretely, and the slope segment 224 may be stored as a mathematical algorithm which is used by the processor 204 (FIG. 10) to compute the appropriate heart rate to be maintained when the determined level of physical activity as measured by the sensor 350 (FIG. 10) falls between the first activity threshold 228 and the second activity threshold 230.

Thus an accelerometer-based, multi-axis physical activity sensor for use with a rate-responsive pacemaker is provided. One skilled in the art will appreciate that the present invention can be practiced by other than the described embodiments, which are presented for purposes of illustration and not of limitation, and the present invention is limited only by the claims which follow.

What is claimed is:

1. A multi-axis physical activity sensor for a rate-responsive pacemaker, comprising:

transducing means for providing a signal indicative of physical activity occurring in directions along a plurality of axes, said transducing means comprising a cantilever beam having a fixed end and a free end, the cantilever beam including a material having an electrical characteristic that varies measurably when said cantilever beam experiences mechanical stresses, the free end deflecting in response to bodily accelerations associated with physical activity, thereby inducing said mechanical stresses in said cantilever beam, said transducing means further comprising a mass disposed on said free end of said cantilever beam and substantially offset with respect to a planar surface of said cantilever beam for imparting multi-axis sensitivity to said sensor;

locking means for securing said mass onto said free end of said cantilever beam; and conducting means for communicating said signal provided by said transducing means to circuitry of said rate-responsive pacemaker.

2. The sensor of claim 1, wherein said transducing means is responsive to physical activity occurring in directions along a plurality of perpendicular axes.

3. The sensor of claim 1, wherein said conducting means comprises a pair of electrical conductors which communicate said signal to said circuitry of said rate-responsive pacemaker.

4. The sensor of claim 1, wherein said locking means comprises a mass mount and a mass backing which lock said mass onto said free end of said cantilever beam.

5. The sensor of claim 1, wherein said material comprises a first film of a piezoelectric polymer that causes electrical potentials to appear across first and second surfaces of said cantilever beam when said cantilever beam experiences said mechanical stresses.

6. The sensor of claim 5, wherein said cantilever beam comprises an electrically conductive beam substrate, and said first film is adhered to a first surface of said beam substrate.

7. The sensor of claim 6, wherein said material further comprises a second film of said piezoelectric polymer adhered to a second surface of said beam substrate.

8. The sensor of claim 1, wherein said conducting means comprises first and second electrically conductive support members which conduct said signal to said circuitry of said rate-responsive pacemaker and mechanically support said cantilever beam so as to prevent said sensor from tipping toward the free end of the cantilever beam when the sensor rests unsecured.

9. The sensor of claim 8, wherein said first and second electrically conductive support members contact, respectively, first and second surfaces of said cantilever beam at said fixed end.

10. The sensor of claim 9, wherein said first and second electrically conductive support members support said cantilever beam so that said cantilever beam is orthogonally oriented with respect to said substrate.

11. The sensor of claim 10, further comprising:
a nonconductive mount that includes a slot within which regions of said first and second electrically conductive support members and said fixed end of said cantilever beam are disposed; and
retaining clip means disposed on said mount for causing said mount to urge said first and second electrically conductive support members against, respectively, said first and second surfaces of said cantilever beam.

12. An accelerometer-based multi-axis physical activity sensor for providing a signal indicative of bodily accelerations associated with physical activity to circuitry of an implantable cardiac stimulating device, said sensor comprising:
a substrate;
means, mounted to said substrate, for providing said signal in accordance with mechanical stresses experienced by said means for providing which are induced by bodily accelerations associated with physical activity, said providing means comprising:
a cantilever beam having a fixed end and a free end, the cantilever beam including a material having an electrical characteristic that varies measurably when said cantilever beam experiences said mechanical stresses, the free end deflecting in response to bodily accelerations associated with physical activity, thereby inducing said mechanical stresses in said cantilever beam;
means, mechanically coupled to said means for providing, for imparting multi-axis sensitivity to said means for providing said imparting means comprising:
a mass disposed on said free end of said cantilever beam and substantially offset with respect to a planar surface of said cantilever beam for imparting multi-axis sensitivity to said sensor; and
locking means for securing said mass onto said free end of said cantilever beam; and
means for conducting said signal from said means for providing to said circuitry of said implantable cardiac stimulating device.

13. The sensor of claim 12, wherein said means for providing is responsive to bodily accelerations associated with physical activity along a plurality of perpendicular axes.

14. The sensor of claim 12, wherein said means for conducting comprises a pair of electrical conductors which communicate said signal to said circuitry of said implantable cardiac stimulating device.

15. The sensor of claim 12, wherein said locking means comprises a mass mount and a mass backing which lock said mass onto said free end of said cantilever beam.

16. The sensor of claim 12, wherein said material comprises a first film of a piezoelectric polymer that causes electrical potentials to appear across first and second surfaces of said cantilever beam when said cantilever beam experiences said mechanical stresses.

17. The sensor of claim 16, wherein said cantilever beam comprises an electrically conductive beam substrate, and said first film is adhered to a first surface of said beam substrate.

18. The sensor of claim 17, wherein said material further comprises a second film of said piezoelectric polymer adhered to a second surface of said beam substrate.

19. The sensor of claim 12, wherein said means for conducting comprises first and second electrically conductive support members which communicate said signal to said circuitry of said implantable cardiac stimulating device and mechanically support said cantilever beam on the substrate.

20. The sensor of claim 19, wherein said first and second electrically conductive support members contact, respectively, first and second surfaces of said cantilever beam at said fixed end.

21. The sensor of claim 20, wherein said first and second electrically conductive support members support said cantilever beam so that said cantilever beam is orthogonally oriented with respect to said substrate.

22. The sensor of claim 21 further comprising:
a nonconductive mount that includes a slot within which regions of said first and second electrically conductive support members and said fixed end of said cantilever beam are disposed; and
retaining clip means disposed on said mount for causing said mount to urge said first and second electrically conductive support members against, respectively, said first and second surfaces of said cantilever beam.

23. A method of fabricating a multi-axis physical activity sensor for use with a rate-responsive pacemaker, comprising the steps of:
forming a transducing element incorporating a material having an electrical characteristic that varies measurably when said transducing element experiences mechanical stresses in response to bodily accelerations associated with physical activity along a plurality of axes comprising the steps of:
fabricating said transducing element in the form of a cantilever beam comprising the steps of:
providing an electrically conductive beam substrate;
adhering a first film of a piezoelectric polymer to a first surface of said beam substrate;
attaching a mass to a first end of said cantilever beam, so as to be substantially offset with respect to a planar surface of said cantilever beam; and
providing a conductive path for communicating a signal representative of said varying electrical characteristic from said transducing element to circuitry of said pacemaker.

24. The method of claim 23, wherein said providing step comprises attaching a pair of electrical conductors to said transducing element, which communicate said signal to said circuitry of said pacemaker.

25. The method of claim 23, wherein said fabricating step further comprises the step of adhering a second film of said piezoelectric polymer to a second surface of said beam substrate.

26. The method of claim 23, wherein said securing step comprises the steps of inserting said second end of said cantilever beam between first and second electrically conductive support members.

27. A rate-responsive pacemaker, comprising:
pulse generating means for generating pacing pulses at an adjustable rate;
control means, coupled to said pulse generating means, for determining the rate at which said pulse generating means generates said pacing pulses in accordance with physical activity; and
transducing means for providing a signal to said control means indicative of physical activity occurring in directions along a plurality of axes, said transducing means comprising a cantilever beam having a fixed end and a free end, the cantilever beam including a material having an electrical characteristic that varies measurably when said cantilever beam experiences mechanical stresses, said material comprising a first film of a piezoelectric polymer that causes electrical potentials to appear across first and second surfaces of said cantilever beam when said cantilever beam experiences mechanical stresses, wherein the free end deflects in response to bodily accelerations associated with physical activity, thereby inducing said mechanical stresses in said cantilever beam, and wherein said transducing means further comprises a mass disposed on said free end of said cantilever beam and substantially offset with respect to a planar surface of said cantilever beam.

28. The pacemaker of claim 21, further comprising a hybrid, and said transducing means is anchored to said hybrid.

29. The pacemaker of claim 27, further comprising a battery support, wherein said transducing means is disposed within said battery support.

30. The pacemaker of claim 27, wherein said cantilever beam comprises an electrically conductive beam substrate, and said first film is adhered to a first surface of said beam substrate.

31. The pacemaker of claim 30, wherein said material further comprises a second film of said piezoelectric polymer adhered to a second surface of said beam substrate.

32. The pacemaker of claim 27, further comprising first and second electrically conductive support members which communicate said signal provided by said transducing means and mechanically support said cantilever beam on a substrate.

33. The pacemaker of claim 32, wherein said first and second electrically conductive support members contact, respectively, first and second surfaces of said cantilever beam at said fixed end.

34. The pacemaker of claim 33, wherein said first and second electrically conductive support members support said cantilever beam so that said cantilever beam is orthogonally oriented with respect to said substrate.

35. The pacemaker of claim 34, further comprising:
a nonconductive mount that includes a slot within which regions of said first and second electrically conductive support members and said fixed end of said cantilever beam are disposed; and
retaining clip means disposed on said mount for causing said mount to urge said first and second electrically conductive support members against, respectively, said first and second surfaces of said cantilever beam.

36. A physical activity sensor for use in a rate-responsive pacemaker comprising:
transducer means for generating a signal indicative of physical activity, comprising a cantilever beam having a fixed end and a free end, the cantilever beam deflecting in response to body accelerations associated with physical activity, thereby inducing mechanical stresses in the cantilever beam, the cantilever beam including a piezoelectric polymer film having first and second surfaces, across which an electrical potential is developed as a function of the mechanical stresses, such electrical potentials furnishing said signal indicative of physical activity, the cantilever beam including a mass disposed on the free end thereof and offset from a planar surface of such cantilever beam for imparting multi-axis sensitivity to the physical activity sensor.

37. The physical activity sensor of claim 36, further comprising conductor means for conducting said signal to desired circuitry in the rate-responsive pacemaker, the conductor means comprising first and second support members, the first and second support members being electrically conductive and in electrical communication with said first and second surfaces, respectively, the support members further for supporting the cantilever beam so as to prevent said sensor from tipping toward the free end of the cantilever beam when the sensor rests unsecured.

38. The physical activity sensor of claim 37, wherein the piezoelectric polymer film comprises first and second piezoelectric polymer films joined together to thereby form a composite piezoelectric polymer film.

39. The physical activity sensor of claim 38, further comprising a beam substrate disposed between the first and second piezoelectric polymer films in sandwich-like fashion.

40. A physical activity sensor for use in a rate-responsive pacemaker comprising:
transducer means for generating a signal indicative of physical activity, comprising a cantilever beam having a fixed end and a free end, the cantilever beam deflecting in response to body accelerations associated with physical activity, thereby inducing mechanical stresses in the cantilever beam, the cantilever beam having first and second surfaces, the cantilever beam including means for generating an electrical potential across said first and second surfaces as a function of the mechanical stresses, such electrical potentials being a measure of said signal indicative of physical activity; and
conductor means for conducting said signal to desired circuitry in the rate responsive pacemaker, the conductor means comprising first and second support members, the first and second support members being electrically conductive and in electrical communication with said first and second surfaces, respectively, the support members further for supporting the cantilever beam so as to prevent said sensor from tipping toward the free end of the cantilever beam when the sensor rests unsecured.

* * * * *